US008513465B2

(12) United States Patent
Kang et al.

(10) Patent No.: US 8,513,465 B2
(45) Date of Patent: Aug. 20, 2013

(54) POTASSIUM ORGANOTRIFLUOROBORATE DERIVATIVE AND A PRODUCTION METHOD THEREFOR

(75) Inventors: Heonjoong Kang, Seongnam-si (KR); Jungyeob Ham, Gangneung-si (KR); Hong Ryul Ahn, Gangneung-si (KR); Young Hee Park, Inje-gun (KR)

(73) Assignee: SNU R&DB Foundation, Seoul (KR)

( * ) Notice: Subject to any disclaimer, the term of this patent is extended or adjusted under 35 U.S.C. 154(b) by 364 days.

(21) Appl. No.: 12/865,979

(22) PCT Filed: Feb. 4, 2009

(86) PCT No.: PCT/KR2009/000532
§ 371 (c)(1),
(2), (4) Date: Aug. 3, 2010

(87) PCT Pub. No.: WO2009/099291
PCT Pub. Date: Aug. 13, 2009

(65) Prior Publication Data
US 2011/0004023 A1    Jan. 6, 2011

(30) Foreign Application Priority Data

Feb. 4, 2008 (KR) .................. 10-2008-0010976

(51) Int. Cl.
*C07F 5/02* (2006.01)
(52) U.S. Cl.
USPC .......................................................... 568/6
(58) Field of Classification Search
USPC .......................................................... 568/6
See application file for complete search history.

(56) References Cited

U.S. PATENT DOCUMENTS
2006/0100465 A1    5/2006    Kabalka

OTHER PUBLICATIONS

Helio A. Stefani et al., 'Recent advances in organotrifluoroborates chemistry', Tetrahedron 63 (2007) 3623-3658.*
Alexander K.L.Yuen, Deprotection of pinacolyl boronate esters via hydrolysis of intermediate potassium trifluoroborates, Tetrahedron Letters 46 (2005) 7899-7903.*
Brown, Allan G.; Crimmin, Michael J.; Edwards, Peter D., Application of the Suzuki biphenyl synthesis to the natural products biphenomycin and vancomycin J. Chem. Soc., Perkin Transactions 1: Organic and Bio-Organic Chemistry (1992), (1), 123-30.*
Stefani at al, "Recent advances in organotrifluoroborates chemistry", Tetrahedron report No. 795, 2007, vol. 63, p. 3623-3658.
Yuen et al., "Deprotection of pinacolyl boronate esters via hydrolysis of intermediate potassium trifluoroborates", Tetrahedron Letters, 2005, vol. 46, p. 7899-7903.
Vedejs et al., "Conversion of Arylboronic Acids into Potassium Aryfitrifluoroborates: Convenient Precursors of Arylboron Difluoride Lewis Acids", J. Org. Chem., 1995, vol. 60, 3020-3027.
Darses at al., "Potassium Organotrifluoroborates: New Partners in Palladium-Catalysed Cross-Coupling Reactions", Eur. J. Org. Chem., 1999, p. 1675-1883.
Molander et al., "Development of the Suzuki-Miyaura Cross-Coupling Reaction: Use of Air-Stable Potassium Alkynyltrifluoroborates in Aryl Alkynylations", J. Org. Chem., 2002, vol. 67, p. 8416-8423.
Miyaura et al., "Palladium-Catalyzed Cross-Coupling Reactions of Organoboron Compounds", Chem. Rev., 1995, vol. 95, p. 2457-2483.
Chemler et al., "The B-Alkyl Suzuki-Miyaura Cross-Coupling Reaction: Development, Mechanisic Study, and Applications in Natural Product Synthesis**", Angew. Chem. Int. Ed., 2001, vol. 40, p. 4544-4568.
Molander et al., "Organotrifluoroborates: Expanding Organoboron Chemistry", Aldrichimica ACTA, 2005, vol. 38, No. 2, p. 49-60.
Molander et al., "Palladium-Catalyzed Suzuki-Miyaura Cross-Coupling Reactions of Potassium Aryl- and Heteroaryltrifluoroborates", J. Org. Chem., 2003, vol. 68, p. 4302-4314.
Molander et al., "Organotrifluoroborates: Protected Boronic Acids That Expand the Versatility of the Suzuki Coupling Reaction", Acc. Chem. Res., 2007, vol. 40, No. 4, p. 275-286.
Molander et al., "Expanding Organoboron Chemistry: Epoxidation of Potassium Organotrifluoroborates", J. Am. Chem. Soc., 2003, vol. 125, p. 11148-11149.
Molander et al., "cis-Dihydroxylation of Unsaturated Potassium Alkyl- and Aryltrifluoroborates", Am. Chem. Soc., 2006, vol. 8, No. 1, p. 75-78.
Molander et al., "Synthesis of Functionalized Organotrifluoroborates via the 1,3-Dipolar Cycloaddition of Azides", Am. Chem. Soc., 2006, vol. 8, No. 13, p. 2767-2770.
Molander et al., "Oxidation of Hydroxyl-Substituted Organotrifluoroborates", J. Am. Chem. Soc., 2006, vol. 128, p. 9634-9635.
Molander et al., "Linchpin Synthons: Metalation of Aryl Bromides Bearing a Potassium Trifluoroborate Moiety", J. Org. Chem., 2006, vol. 71, p. 7491-7493.
Molander et al., "Synthesis of Unsaturated Organotrifluoroborates via Wittig and Horner—Wadsworth—Emmons Olefination", J. Org. Chem., 2006, vol. 71, p. 6135-6140.
Molander et al., "Preparation and Wittig Reactions of Organotrifluoroborato Phosphonium Ylides", Organic Letters, 2007, vol. 9, No. 5, p. 821-824.
Molander et al., "Ozonolysis of Unsaturated Organotrifluoroborates", J. Org. Chem., 2007, vol. 72, p. 3558-3560.

* cited by examiner

*Primary Examiner* — Johann R Richter
*Assistant Examiner* — Kofi Adzamli
(74) *Attorney, Agent, or Firm* — The Webb Law Firm

(57) ABSTRACT

Provided are a production method for a potassium organotrifluoroborate compound having a hydroxyl group, and a novel potassium organotrifluoroborate compound having a hydroxyl group. The production method is advantageous in that a potassium organotrifluoroborate compound can be produced in a single reaction without recourse to a process of isolating and purifying an intermediate. The novel potassium organotrifluoroborate compound having a hydroxyl group is useful as a reactant which is widely used in the total synthesis of physiologically active natural products and diverse organic synthesis reactions including halogen substitution reactions, 1,2- and 1,4-addition reactions using a rhodium (Rh) catalyst, and Suzuki coupling reactions using a palladium (Pd) catalyst.

11 Claims, No Drawings

US 8,513,465 B2

POTASSIUM ORGANOTRIFLUOROBORATE DERIVATIVE AND A PRODUCTION METHOD THEREFOR

CROSS-REFERENCE TO RELATED APPLICATIONS

This application claims priority under 35 U.S.C. §119 to Korean Patent Application No. 10-2008-0010976, filed on Feb. 4, 2008, in the Korean Intellectual Property Office, the disclosure of which is incorporated herein by reference in its entirety.

TECHNICAL FIELD

The following disclosure relates to a novel potassium organotrifluoroborate compound having a hydroxyl group, which may be widely used in diverse organic synthesis reactions including Suzuki coupling reactions using a palladium (Pd) catalyst, 1,2- and 1,4-addition reactions using a rhodium (Rh) catalyst and halogen substitution reactions, and total synthesis of physiologically active natural products, and a method for preparing the same.

BACKGROUND

Recently, various carbon-carbon coupling reactions using metal catalysts are reported in the field of organic chemistry. The advancement in the organometallic chemistry has enabled total synthesis of land and marine natural products of very complex structure, which had been impossible with the artificial synthesis. In particular, the carbon-carbon coupling reaction using boron, developed by Professors Suzuki and Miyaura, gives more environment-friendly and less harmful products than other reactions using zinc, tin or magnesium. Since the reaction is more stable (e.g., water is used in the reaction) and easily applicable to various fields (total synthesis of natural products, medicinal chemistry, polymer synthesis, etc.), studies are actively carried out thereabout (*Chem. Rev.* 1995, 95, 2457; *Angew. Chem., Int. Ed.* 2001, 40, 4544). Usually, the Suzuki coupling reaction is performed using a palladium (Pd) organometallic catalyst. Formerly, organoboronic acids or organoboronate esters were used as starting material. However, because the organoboronic acid or the organoboronate ester tends to form a dimer or a trimer, a quantitative reaction is difficult. In addition, there is a problem of recovering the expensive ligand such as catechol, pinacol, diethanolamine, etc., which is used to stabilize the organoboronate ester. Further, the reactants are easily attacked by a Lewis base or other common nucleophile to lead to side reactions. On the contrary, potassium organotrifluoroborates are tolerant to air and moisture, and may be prepared easily by adding inexpensive potassium hydrogen fluoride ($KHF_2$) to the organoboronic acid or the organoboronate ester. In addition, since there is no significant difference in reactivity for the Suzuki, the carbon-carbon coupling using potassium organotrifluoroborates will be utilized in many fields (*Aldrichimica Acta* 2005, 38, 49; *J. Org. Chem.* 2003, 4313; *Acc. Chem. Res.* 2007, 40, 275; *Tetrahedron* 2007, 63, 3623).

Sigma-Aldrich, the world's leading reagent producing company, is selling more than 30 potassium organotrifluoroborates. Other dozen small- or large-sized reagent companies are also producing potassium organotrifluoroborates used in the field of combinatorial chemistry or medicinal chemistry in small quantities. These compounds are expected to replace the organoboronic acids or the organoboronate esters for the Suzuki coupling reactions. However, in spite of the potential demand, the currently available potassium organotrifluoroborates are not enough to satisfy the needs. Recently, various derivatives of potassium organotrifluoroborate and simple methods for preparing them are reported (*J. Am. Chem. Soc.* 2003, 125, 11148; *Org. Lett.* 2006, 8, 75; *Org. Lett.* 2006, 8, 2767; *J. Am. Chem. Soc.* 2006, 128, 9634; *J. Org. Chem.* 2006, 71, 749; *J. Org. Chem.* 2006, 71, 6135; *Org. Lett.* 2007, 9, 821; *J. Org. Chem.* 2007, 72, 3558). However, more researches are required.

In this regard, development of novel potassium organotrifluoroborate derivatives is important in drug developments based on synthesis of various organic products and physiologically active natural products to easily synthesize sensitive or complicated substances.

With all the usefulness, the potassium organotrifluoroborate compounds have the following drawbacks in the preparation method thereof.

(1) Usually, the potassium organotrifluoroborate compounds are prepared from relatively expensive organoboronic acids or organoboronate esters as starting material.

(2) In Scheme 1, in order to synthesize the organoboronic acid or organoboronate ester having an alcohol group, a complicated process of protecting the hydroxyl group before and the lithium-halogen exchange reaction and then removing the protecting group is required.

(3) In Scheme 1, the silyl ($-SiR_3$) compounds used to protect the hydroxyl group are relatively expensive. Accordingly, the existing potassium organotrifluoroborate synthesis method is uneconomical.

(4) Since the organoboronic acid or organoboronate ester compound in Scheme 1 tends to form a polymer easily in the air, there are problems in purification, storage and quantitative reaction.

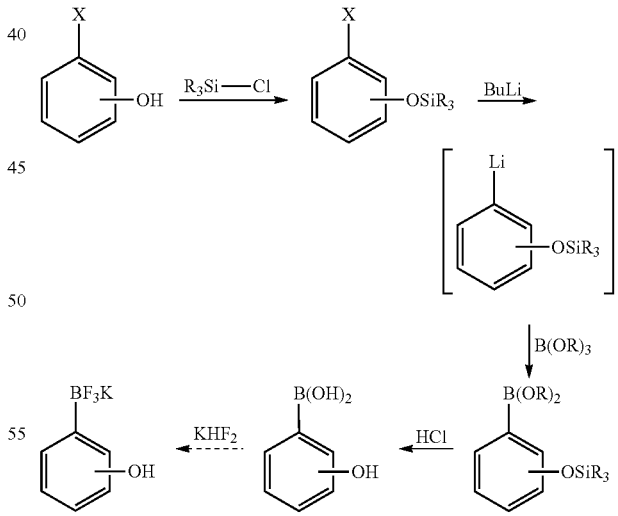

[Scheme 1]

Accordingly, a simple, inexpensive and fast method for preparing a potassium organotrifluoroborate having a hydroxyl group is needed.

SUMMARY

The present invention is directed to providing a convenient and economical method for preparing a potassium organotrifluoroborate salt compound having a hydroxyl group represented by Chemical Formula 1 via a single reaction from an aryl halide compound, without recourse to a process of isolating and purifying an intermediate.

The present invention is also directed to providing a novel potassium organotrifluoroborate compound having a hydroxyl group which may be widely used in diverse organic synthesis reactions including Suzuki coupling reactions using a palladium (Pd) catalyst, 1,2- and 1,4-addition reactions using a rhodium (Rh) catalyst and halogen substitution reactions, and total synthesis of physiologically active natural products, and a method for preparing the same.

The inventors of the present invention have worked to solve the aforesaid problems. As a result, they have found out that, as illustrated in Scheme 2, a potassium organotrifluoroborate compound represented by Chemical Formula 1 is prepared from a 3-step reaction process of reacting an aryl halide compound having a hydrogen-donating hydroxyl group represented by Chemical Formula 2 with an organometallic reagent so as to protect the hydrogen-donating group and perform halogen-lithium exchange at once [Step A-1], subsequently reacting with a borate compound $(B(OR^2)_3)$ [Step A-2] and then reacting with potassium hydrogen fluoride $(KHF_2)$ without an isolation process [Step A-3], or from a 2-step reaction process of reacting a mixture of the compound represented by Chemical Formula 2 and a borate compound $(B(OR^2)_3)$ with an organometallic reagent [Step A-4] and then subsequently reacting with potassium hydrogen fluoride $(KHF_2)$.

[Scheme 2]

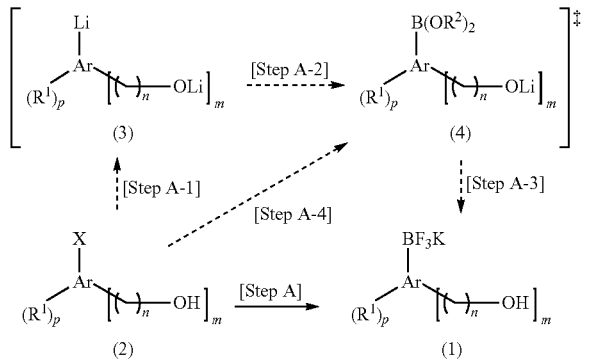

In an aspect, the present invention provides a method for preparing a potassium organotrifluoroborate compound represented by Chemical Formula 1, including: a) reacting a compound represented by Chemical Formula 2 with an organolithium reagent to prepare a compound represented by Chemical Formula 3; b) reacting the compound represented by Chemical Formula 3 with a borate compound represented by Chemical Formula 5 to prepare a compound represented by Chemical Formula 4; and c) reacting the compound represented by Chemical Formula 4 with potassium hydrogen fluoride to prepare the compound represented by Chemical Formula 1.

Preferably, the steps proceed successively without isolation of intermediates, i.e. the compound represented by Chemical Formula 3 and the compound represented by Chemical Formula 4.

In another aspect, the present invention provides a method for preparing a potassium organotrifluoroborate compound represented by Chemical Formula 1, including: a) reacting a mixture of a compound represented by Chemical Formula 2 and a borate compound represented by Chemical Formula 5 with an organolithium reagent to prepare a compound represented by Chemical Formula 4; and b) reacting the compound represented by Chemical Formula 4 with potassium hydrogen fluoride to prepare the compound represented by Chemical Formula 1:

Preferably, the steps proceed successively without isolation of an intermediate, i.e. the compound represented by Chemical Formula 4.

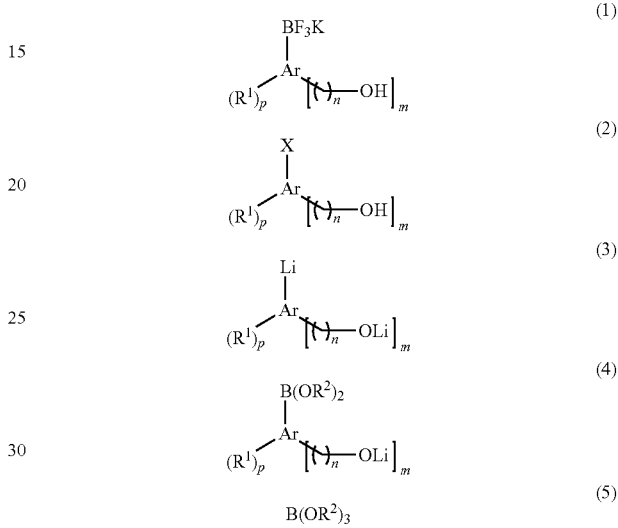

In Chemical Formulae 1 to 5, Ar is selected from phenylene, biphenylene, or naphthylene; $R^1$ is independently selected from $C_1$-$C_7$ alkyl, $C_1$-$C_7$ alkyloxy, $C_1$-$C_7$ allcylthioxy, hydroxyphenyl, hydroxynaphthyl or halogen; $R^2$ is selected from $C_1$-$C_7$ alkyl or phenyl; X is selected from bromine or iodine; in is an integer selected from 1 to 3; n is an integer selected from 0 to 4; and p is an integer selected from 0 to 4.

In another aspect, the present invention provides a novel potassium organotrifluoroborate compound having a hydroxyl group represented by Chemical Formula 6.

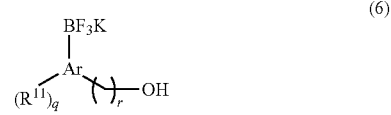

In Chemical Formula 6, Ar is selected from phenylene, biphenylene or naphthylene; $R^{11}$ is independently is selected from $C_1$-$C_7$ alkyl or halogen; r is an integer selected from 0 to 2; and q is an integer selected from 0 to 2.

Specific examples of the novel potassium organotrifluoroborate compound having a hydroxyl group represented by Chemical Formula 6 include potassium 2-hydroxyphenyltrifluoroborate, potassium 3-hydroxyphenyltrifluoroborate, potassium 4-hydroxyphenyltrifluoroborate, potassium 4'-hydroxy-[1,1'-biphenyl]-4-trifluoroborate, potassium 6-hydroxy-2-naphthalenetrifluoroborate, potassium 4-hydroxy-3, 5-dimethylphenyltrifluoroborate, potassium 4-hydroxy-3-methylphenyltrifluoroborate, potassium 3-chloro-4-hydroxyphenyltrifluoroborate, potassium 2-(hydroxymethyl)phenyltrifluoroborate, potassium 3-(hydroxymethyl)phenyltrifluoroborate, potassium 4-(hydroxymethyl)phenyltrifluoroborate, potassium 2-(2-hydroxyethyl)phenyltrifluoroborate, potassium 3-(2-hydroxyethyl)phenyltrifluoroborate, potassium 4-(2-hydroxyethyl)phenyltrifluoroborate, or the like.

DETAILED DESCRIPTION OF EMBODIMENTS

The advantages, features and aspects of the present invention will become apparent from the following description of the embodiments with reference to the accompanying drawings, which is set forth hereinafter. The present invention may, however, be embodied in different forms and should not be construed as limited to the embodiments set forth herein. Rather, these embodiments are provided so that this disclosure will be thorough and complete, and will fully convey the scope of the present invention to those skilled in the art. The terminology used herein is for the purpose of describing particular embodiments only and is not intended to be limiting of example embodiments. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Hereinafter, the preparation method according to the present invention will be described in detail.

The preparation method according to the present invention allows preparation of the Potassium organotrifluoroborate salt compound represented by Chemical Formula 1 via a single reaction without recourse to a process of isolating and purifying an intermediate. Specifically, as shown in Scheme 2, the preparation method may comprise a 3-step process or a 2-step process. The 3-step process comprises protecting the hydroxyl group of the compound represented by Chemical Formula 2 and performing halogen-lithium exchange using an organolithium reagent at once, subsequently reacting with the borate compound represented by Chemical Formula 5, and then reacting with potassium hydrogen fluoride and terminating the reaction using distilled water to prepare the potassium organotrifluoroborate compound represented by Chemical Formula 1. And, the 2-step process comprises reacting a mixture of the compound represented by Chemical Formula 2 and the borate compound represented by Chemical Formula 5 with an organolithium reagent, and then reacting with potassium hydrogen fluoride and terminating the reaction using distilled water to prepare the potassium organotrifluoroborate compound represented by Chemical Formula 1. The compound represented by Chemical Formula 2 used as a starting material in the present invention is a known, easily available compound.

A shown in Scheme 2, the preparation method according to the present invention provides a single reaction without recourse to a process of isolating and purifying an intermediate, comprising the 3-step or 2-step process. Hereinafter, each step will be described in detail.

[3-Step Reaction Process]
[Step A-1]

For the preparation of the compound represented by Chemical Formula 3, one or more anhydrous solvent(s) selected from diethyl ether, tetrahydrofuran, hexane, heptane, etc. is used. Among them, diethyl ether, tetrahydrofuran or a mixture of diethyl ether and tetrahydrofuran is preferred.

The organolithium reagent used for the protection of the hydroxyl group and the halogen-metal exchange may be n-butyllithium, sec-butyllithium, tert-butyllithium, or the like. Among them, tert-butyllithium is preferred. It may be used in an amount of 2 to 5 equivalents. Preferably, n-butyllithium or sec-butyllithium is used in an amount of 2.0 to 2.2 equivalents, and t-butyllithium is used in an amount of 3.0 to 3.2 equivalents. If the organolithium reagent is used in an amount less than 2.0 equivalents, the hydroxyl group is protected well but the halogen-metal exchange may be incomplete. As a result, the yield of the desired organotrifluoroborate is decreased. And, if the organolithium reagent used in an excess amount, byproducts such as potassium n-butyltrifluoroborate, potassium sec-butyltrifluoroborate, potassium t-butyltrifluoroborate, etc. are produced along with the desired product.

The reaction temperature may be different depending on the solvent used. Usually, the reaction is performed at −78 to −10° C., preferably at −78 to −40° C. The reaction time may be different depending on the reaction temperature and the solvent used. Usually, the reaction is performed for 10 minutes to 240 minutes, preferably for 30 minutes to 90 minutes.

[Step A-2]

The borate compound represented by Chemical Formula 5 reacted with the compound represented by Chemical Formula 3 may be a trialkylborate reagent such as trimethylborate $(B(OCH_3)_3)$, triethylborate $(B(OCH_2CH_3)_3)$, tripropylborate $(B(OCH_2CH_2CH_3)_3)$, triisopropylborate $(B(O-^iPr)_3)$, triisobutylborate $(B(OCH_2-^iPr)_3)$, triphenylborate $(B(OPh)_3)$, etc. Among them, triisopropylborate is preferred. The borate compound represented by Chemical Formula 5 may be used in an amount of 0.9 to 3 equivalents, preferably 0.95 to 1 equivalent. If the borate compound is used in an amount less than 0.9 equivalent, the yield of the desired organotrifluoroborate is low. And, if it is used in an amount exceeding 3.0 equivalents, it is difficult to obtain a pure product because of increased byproduct production.

The reaction temperature may be different depending on the solvent and the organolithium reagent used. Usually, the reaction is performed at −78 to 0° C. Preferably, the temperature is maintained at −75° C. during the addition of the borate compound represented by Chemical Formula 5, and then slowly increased from −75° C. to progress the reaction. The reaction may be performed for 30 minutes to 1 day, preferably for 30 minutes to 90 minutes.

[Step A-3]

The compound represented by Chemical Formula 4 is reacted with potassium hydrogen fluoride, and then the reaction is terminated by adding distilled water. After the solvent is completely removed by distillation under reduced pressure, one or more solvent(s) selected from anhydrous acetone, anhydrous methanol, anhydrous ethanol, anhydrous acetonitrile, etc. is added to dissolve the product. Then, the undissolved salt is removed using celite. Removal of the solvent from the filtered product under reduced pressure gives the compound represented by Chemical Formula 1.

Potassium hydrogen fluoride is used in an amount of 2 to 10 equivalents, preferably 3 to 5 equivalents. If potassium hydrogen fluoride is used in an amount less than 2.0 equivalents, the yield of the organotrifluoroborate decreases because of insufficient fluoride. And, if potassium hydrogen fluoride is used in an amount exceeding 10 equivalents, removal of moisture and purification becomes difficult. The mixture solution is adjusted to pH 4 or lower, specifically to pH 1 to 4. If the pH of the mixture solution exceeds 4, the crystal structure of the organotrifluoroborate may be unsatisfactory. The reaction is performed at 0 to 25° C. for 10 to 60 minutes.

[2-Step Reaction Process]

[Step A-4]

The compound represented by Chemical Formula 2 and the borate compound represented by Chemical Formula 5 are dissolved in an anhydrous solvent, and an organolithium reagent is added to perform the protection of the alcohol group and the halogen-lithium exchange at once.

The borate compound represented by Chemical Formula 5 used in this step may be a trialkylborate reagent such as trimethylborate, triethylborate, tripropylborate, triisopropylborate, triisobutylborate, triphenylborate, etc. Among them, triisopropylborate is preferred. The trialkylborate compound may be used in an amount of 0.9 to 3 equivalents, preferably 0.95 to 1 equivalent.

The organolithium reagent used for the protection of the hydroxyl group and the halogen-metal exchange may be n-butyllithium, sec-butyllithium, tert-butyllithium, or the like. Among them, tert-butyllithium is preferred. It may be used in an amount of 2 to 5 equivalents. Preferably, n-butyllithium or sec-butyllithium is used in an amount of 2.0 to 2.2 equivalents, and t-butyllithium is used in an amount of 3.0 to 3.2 equivalents.

The reaction temperature may be different depending on the solvent and the organolithium reagent used. Usually, the reaction is performed at −78 to 0° C. Preferably, the temperature is maintained at −75° C. during the addition of the borate compound represented by Chemical Formula 5, and then slowly increased from −75° C. to progress the reaction. The reaction may be performed for 30 minutes to 1 day, preferably for 30 minutes to 90 minutes.

[Step A-3]

The compound represented by Chemical Formula 4 is reacted with potassium hydrogen fluoride, and then the reaction is terminated by adding distilled water. After the solvent is completely removed by distillation under reduced pressure, one or more solvent(s) selected from anhydrous acetone, anhydrous methanol, anhydrous ethanol, anhydrous acetonitrile, etc. is added to dissolve the product. Then, the undissolved salt is removed using celite. Removal of the solvent from the filtered product under reduced pressure gives the compound represented by Chemical Formula 1.

Potassium hydrogen fluoride is used in an amount of 2 to 10 equivalents, preferably 3 to 5 equivalents. The mixture solution is adjusted to pH 4 or lower, specifically to pH 1 to 4. The reaction is performed at 0 to 25° C. for 10 to 60 minutes.

EXAMPLES

The examples and experiments will now be described. The following examples and experiments are for illustrative purposes only and not intended to limit the scope of this disclosure.

Example 1

Synthesis of Potassium 2-hydroxyphenyltrifluoroborate (3-Step Process)

2-Iodophenol (220 mg, 1.0 mmol) was dissolved in anhydrous tetrahydrofuran (8 mL) under nitrogen atmosphere and kept at −78° C. After slowly adding tert-butyllithium (1.77 mL, 1.7 M pentane solution, 3 equivalents) dropwise for 10 minutes, reaction was further carried out at the same temperature for 30 minutes. After slowly adding triisopropylborate (188 mg, 1.0 mmol) dropwise for 15 minutes, the mixture was heated to −30° C. over 1 hour. After adding potassium hydrogen fluoride (273 mg, 3.5 mmol, 3.5 equivalents) and distilled water (4 mL) to terminate the reaction, the resulting mixture was vigorously stirred at room temperature. 30 minutes later, after completely removing the solvent using a vacuum distiller, moisture was completely removed under high vacuum. The residue was dissolved in anhydrous acetone (8 mL) and the undissolved salt was removed from acetone using celite. The filtered product was concentrated and then precipitated by adding ether (Et$_2$O, 10 mL). Thus obtained white crystal was filtered and then dried. Potassium 2-hydroxyphenyltrifluoroborate (154 mg, yield=77%) was yielded.

$^1$H NMR (500 MHz, DMSO-d$_6$) δ 7.37 (q, 1H, —OH, J=9.1 Hz), 7.11 (dd, 1H, J=7.0, 1.0 Hz), 6.91 (td, 1H, J=7.6, 1.6 Hz), 6.58 (t, 1H, J=7.1 Hz), 6.49 (d, 1H, J=8.0 Hz).

$^{13}$C NMR (126 MHz, DMSO-d$_6$) δ 159.9, 133.6, 127.6, 119.0, 114.0.

Example 2

Synthesis of Potassium 2-hydroxyphenyltrifluoroborate (2-Step Process)

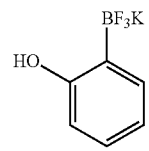

2-Iodophenol (220 mg, 1.0 mmol) and triisopropylborate (188 mg, 1.0 mmol) were dissolved in anhydrous tetrahydrofuran (8 mL) under nitrogen atmosphere and kept at −78° C. After slowly adding tert-butyllithium (1.77 mL, 1.7 M pentane solution, 3 equivalents) dropwise for 10 minutes, reaction was further carried out at the same temperature for 40 minutes. Then, the mixture was slowly heated to −30° C. over 1 hour. After adding potassium hydrogen fluoride (273 mg, 3.5 mmol, 3.5 equivalents) and distilled water (4 mL) to terminate the reaction, the resulting mixture was vigorously stirred at room temperature. 30 minutes later, after completely removing the solvent using a vacuum distiller, moisture was completely removed under high vacuum. The residue was dissolved in anhydrous acetone (8 mL) and the undissolved salt was removed from acetone using celite. The filtered product was concentrated and then precipitated by adding ether (Et$_2$O, 10 mL). Thus obtained white crystal was filtered and then dried. The target compound (130 mg, yield=65%) was yielded.

Example 3

Synthesis of Potassium 3-hydroxyphenyltrifluoroborate (3-Step Process)

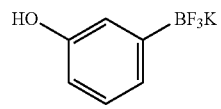

Reaction was performed in the same manner as Example 1 except for using 3-iodophenol (220 mg, 1.0 mmol) instead of 2-iodophenol. Purification yielded the target compound (196 mg, yield=98%).

$^1$H NMR (500 MHz, CD$_3$OD) δ 7.04 (t, 1H, J=7.5 Hz), 6.98 (m, 2H), 6.61 (dd, 1H, J=7.5, 2.5 Hz).

$^{13}$C NMR (126 MHz, CD$_3$OD) δ 155.8, 127.9, 122.8, 117.9, 113.0.

Example 4

Synthesis of Potassium 3-hydroxyphenyltrifluoroborate (2-Step Process)

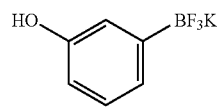

Reaction was performed in the same manner as Example 2 except for using 3-iodophenol (220 mg, 1.0 mmol) instead of 2-iodophenol. Purification yielded the target compound (172 mg, yield=86%).

Example 5

Synthesis of Potassium 4-hydroxyphenyltrifluoroborate (3-Step Process)

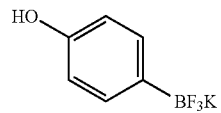

Reaction was performed in the same manner as Example 1 except for using 4-iodophenol (220 mg, 1.0 mmol) instead of 2-iodophenol. Purification yielded the target compound (196 mg, yield=98%).

$^1$H NMR (500 MHz, acetone-d$_6$+DMSO-d$_6$) δ 7.98 (br s, 1H), 7.29 (d, 2H, J=7.5 Hz), 6.60 (d, 2H, J=8.0 Hz).

$^{13}$C NMR (126 MHz, acetone-d$_6$+DMSO-d$_6$) δ 155.6, 132.7, 113.5.

Example 6

Synthesis of Potassium 4-hydroxyphenyltrifluoroborate (2-Step Process)

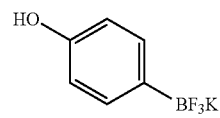

Reaction was performed in the same manner as Example 2 except for using 4-iodophenol (220 mg, 1.0 mmol) instead of 2-iodophenol. Purification yielded the target compound (146 mg, yield=73%).

Example 7

Synthesis of Potassium 4-hydroxyphenyltrifluoroborate (3-Step Process)

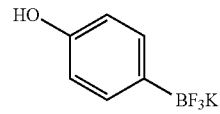

Reaction was performed in the same manner as Example 1 except for using 4-bromophenol (173 mg, 1.0 mmol) instead of 2-iodophenol. Purification yielded the target compound (122 mg, yield=61%).

Example 8

Synthesis of Potassium 4-hydroxy-[1,1-biphenyl]-4-trifluoroborate

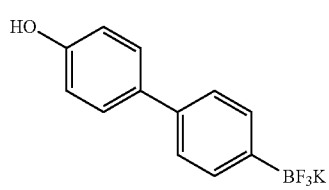

Reaction was performed in the same manner as Example 1 except for using 4-bromo-[1,1-biphenyl]-4-ol (249.1 mg, 1.0 mmol) instead of 2-iodophenol. Purification yielded the target compound (102 mg, yield=37%).

$^1$H NMR (500 MHz, acetone-d$_6$+DMSO-d$_6$) δ 8.99 (br s, 1H), 7.52 (d, 2H, J=8.0 Hz), 7.42 (d, 2H, J=8.5 Hz), 7.32 (d, 2H, J=7.5 Hz), 6.86 (d, 2H, J=8.5 Hz).

$^{13}$C NMR (126 MHz, acetone-d$_6$+DMSO-d$_6$) δ 157.0, 137.7, 133.6, 132.3, 127.6, 124.4, 115.7.

Example 9

Synthesis of Potassium 4-hydroxy-[1,1-biphenyl]-4-trifluoroborate

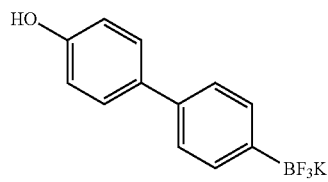

Reaction was performed in the same manner as Example 1 except for using 4-iodo-[1,1-biphenyl]-4-ol (296.1 mg, 1.0 mmol) instead of 2-iodophenol. Purification yielded the target compound (238 mg, yield=86%).

Example 10

Synthesis of Potassium 6-hydroxy-2-naphthalenetrifluoroborate

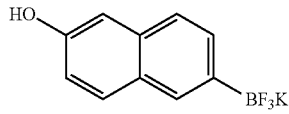

Reaction was performed in the same manner as Example 1 except for using 6-bromo-2-naphthol (223 mg, 1.0 mmol) instead of 2-iodophenol. Purification yielded the target compound (190 mg, yield=76%).

$^1$H NMR (500 MHz, acetone-d$_6$) δ 8.19 (s, 1H), 7.84 (s, 1H), 7.60 (d, 1H, J=3.7 Hz), 7.59 (d, 1H, J=8.1 Hz), 7.43 (d, 1H, J=8.1 Hz), 7.07 (d, 1H, J=2.4 Hz), 6.99 (dd, 1H, J=8.8, 2.5 Hz).

$^{13}$C NMR (126 MHz, acetone-d$_6$) δ 154.0, 134.1, 131.6, 130.1, 129.3, 128.8, 123.7, 116.8, 108.8.

Example 11

Synthesis of Potassium 4-hydroxy-3,5-dimethylphenyltrifluoroborate

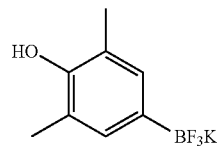

Reaction was performed in the same manner as Example 1 except for using 4-bromo-2,6-dimethylphenol (201 mg, 1.0 mmol) instead of 2-iodophenol. Purification yielded the target compound (148 mg, yield=65%).

$^1$H NMR (500 MHz, acetone-d$_6$) δ 6.89 (s, 2H), 6.33 (s, 1H), 2.02 (s, 6H).

$^{13}$C NMR (126 MHz, acetone-d$_6$) δ 151.2, 132.3, 121.1, 114.9, 16.0.

Example 12

Synthesis of Potassium 4-hydroxy-3-methylphenyltrifluoroborate

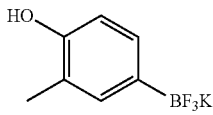

Reaction was performed in the same manner as Example 1 except for using 4-bromo-2-methylphenol (187 mg, 1.0 mmol) instead of 2-iodophenol. Purification yielded the target compound (163 mg, yield=76%).

$^1$H NMR (500 MHz, acetone-d$_6$) δ 7.36 (s, 1H), 7.19 (s, 1H), 7.12 (d, 1H, J=7.5 Hz), 6.57 (d, 1H, J=7.5 Hz), 2.15 (s, 3H).

$^{13}$C NMR (126 MHz, acetone-d$_6$) δ 153.4, 134.6, 130.2, 121.3, 113.2, 15.7.

Example 13

Synthesis of Potassium 4-hydroxy-3-methylphenyltrifluoroborate

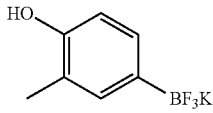

Reaction was performed in the same manner as Example 1 except for using 4-iodo-2-methylphenol (234 mg, 1.0 mmol) instead of 2-iodophenol. Purification yielded the target compound (208 mg, yield=97%).

Example 14

Synthesis of Potassium 3-chloro-4-hydroxyphenyltrifluoroborate

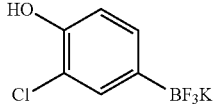

Reaction was performed in the same manner as Example 1 except for using 4-bromo-2-chlorophenol (207.5 mg, 1.0 mmol) instead of 2-iodophenol. Purification yielded the target compound (209 mg, yield=89%).

$^1$H NMR (500 MHz, acetone-d$_6$) δ 7.89 (br s, 1H), 7.36 (s, 1H), 7.22 (d, 1H, J=7.5 Hz), 6.77 (d, 1H, J=7.5 Hz).

$^{13}$C NMR (126 MHz, acetone-d$_6$) δ 150.5, 132.9, 131.3, 118.7, 115.3.

Example 15

Synthesis of Potassium 2-(hydroxymethyl)phenyltrifluoroborate

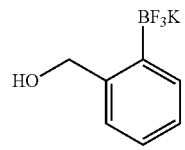

Reaction was performed in the same manner as Example 1 except for using 2-bromobenzyl alcohol (187 mg, 1.0 mmol) instead of 2-iodophenol. Purification yielded the target compound (128 mg, yield=60%).
$^1$H NMR (500 MHz, acetone-d$_6$) δ 7.54 (m, 1H), 7.11 (m, 1H), 7.01 (m, 2H), 4.64 (s, 2H), 3.63 (br s, 1H).
$^{13}$C NMR (126 MHz, acetone-d$_6$) δ 145.2, 132.6, 127.3, 125.4, 125.3, 65.8.

Example 16

Synthesis of Potassium 3-(hydroxymethyl)phenyltrifluoroborate

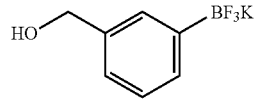

Reaction was performed in the same manner as Example 1 except for using 3-bromobenzyl alcohol (187 mg, 1.0 mmol) instead of 2-iodophenol. Purification yielded the target compound (178 mg, yield=83%).
$^1$H NMR (500 MHz, acetone-d$_6$) δ 7.45 (s, 1H), 7.36 (t, 1H, J=4.5 Hz), 7.07 (d, 2H, J=4.5 Hz), 4.53 (d, 2H, J=6.0 Hz), 3.82 (t, 1H, J=6.0 Hz).
$^{13}$C NMR (126 MHz, acetone-d$_6$) δ 139.8, 130.6, 130.5, 126.3, 124.1, 65.2.

Example 17

Synthesis of Potassium 4-(hydroxymethyl)phenyltrifluoroborate

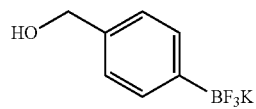

Reaction was performed in the same manner as Example 1 except for using 4-bromobenzyl alcohol (187 mg, 1.0 mmol) instead of 2-iodophenol. Purification yielded the target compound (193 mg, yield=90%).
$^1$H NMR (500 MHz, acetone-d$_6$) δ 7.44 (d, 2H, J=7.5), 7.10 (d, 2H, J=7.5 Hz), 4.54 (d, 2H, J=6.0 Hz), 3.83 (t, 1H, J=6.0 Hz).

$^{13}$C NMR (126 MHz, acetone-d$_6$) δ 139.0, 131.6, 125.2, 64.8.

Example 18

Synthesis of Potassium 2-(2-hydroxyethyl)phenyltrifluoroborate

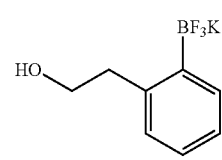

Reaction was performed in the same manner as Example 1 except for using 2-bromophenethyl alcohol (201 mg, 1.0 mmol) instead of 2-iodophenol. Purification yielded the target compound (116 mg, yield=51%).
$^1$H NMR (500 MHz, acetone-d$_6$) δ 7.43 (m, 1H), 6.97 (m, 2H), 6.88 (m, 1H), 3.90 (t, 2H, J=5.5 Hz), 2.65 (t, 2H, J=5.5 Hz).
$^{13}$C NMR (126 MHz, acetone-d$_6$) δ 143.2, 131.4, 126.0, 125.4, 124.7, 61.7, 34.1.

Example 19

Synthesis of Potassium 3-(2-hydroxyethyl)phenyltrifluoroborate

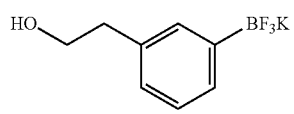

Reaction was performed in the same manner as Example 1 except for using 3-bromophenethyl alcohol (201 mg, 1.0 mmol) instead of 2-iodophenol. Purification yielded the target compound (155 mg, yield=68%).
$^1$H NMR (500 MHz, acetone-d$_6$) δ 7.37 (s, 1H), 7.33 (d, 1H, J=7.5 Hz), 7.04 (t, 1H, J=7.5 Hz), 6.94 (d, 1H, J=7.5 Hz), 3.71 (q, 2H, J=7.0 Hz), 3.58 (t, 1H, J=5.5 Hz), 2.75 (t, 2H, J=7.0 Hz).
$^{13}$C NMR (126 MHz, acetone-d$_6$) δ 136.8, 132.5, 129.6, 126.6, 126.2, 63.8, 40.2.

Example 20

Synthesis of Potassium 4-(2-hydroxyethyl)phenyltrifluoroborate

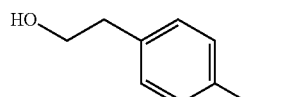

Reaction was performed in the same manner as Example 1 except for using 4-bromophenethyl alcohol (201 mg, 1.0 mmol) instead of 2-iodophenol. Purification yielded the target compound (166 mg, yield=73%).

$^1$H NMR (500 MHz, acetone-d$_6$) δ 7.40 (d, 2H, J=7.5 Hz), 6.98 (d, 2H, J=7.5 Hz), 3.70 (q, 2H, J=7.5 Hz), 3.54 (t, 1H, J=5.5 Hz), 2.74 (t, 2H, J=7.5 Hz).
$^{13}$C NMR (126 MHz, acetone-d$_6$) δ 135.9, 131.8, 127.2, 63.8, 39.9.

The present invention enables a convenient and economical preparation of a potassium organotrifluoroborate compound having a hydroxyl group. The potassium organotrifluoroborate compound may be widely used in diverse organic synthesis reactions including Suzuki coupling reactions using a palladium (Pd) catalyst, 1,2- and 1,4-addition reactions using a rhodium (Rh) catalyst and halogen substitution reactions, and total synthesis of physiologically active natural products.

Since an aryl group having a hydroxyl group serves as an important functional group in flavonoids of land natural products and physiologically active ingredients in marine natural products, the potassium organotrifluoroborate compound represented by Chemical Formula 1 has a great commercial potential in total synthesis of physiologically active natural products and synthesis of their derivatives and diverse organic synthesis reactions including drug development, replacing existing unstable organoboronic acids or organoboronate esters.

While the present invention has been described with respect to the specific embodiments, it will be apparent to those skilled in the art that various changes and modifications may be made without departing from the spirit and scope of the invention as defined in the following claims.

What is claimed is:

1. A method for preparing a potassium organotrifluoroborate compound represented by Chemical Formula 1, comprising:
reacting a compound represented by Chemical Formula 2 with an organolithium reagent to prepare a compound represented by Chemical Formula 3;
reacting the compound represented by Chemical Formula 3 with a borate compound represented by Chemical Formula 5 to prepare a compound represented by Chemical Formula 4; and
reacting the compound represented by Chemical Formula 4 with potassium hydrogen fluoride to prepare the compound represented by Chemical Formula 1:

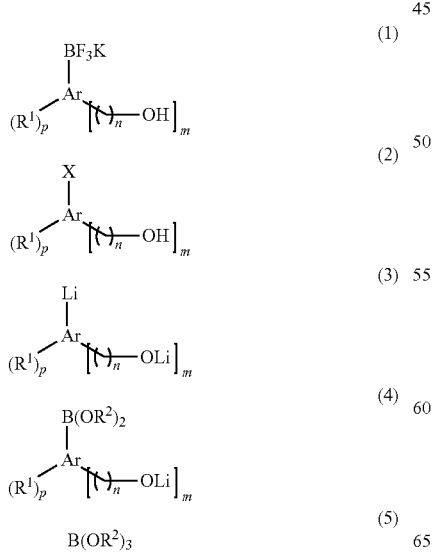

wherein
Ar is selected from phenylene, biphenylene, or naphthylene;
R$^1$ is independently selected from C$_1$-C$_7$ alkyl, C$_1$-C$_7$ alkyloxy, C$_1$-C$_7$ alkylthioxy, hydroxyphenyl, hydroxynaphthyl or halogen;
R$^2$ is selected from C$_1$-C$_7$ alkyl or phenyl;
X is selected from bromine or iodine;
m is an integer selected from 1 to 3;
n is an integer selected from 0 to 4; and
p is an integer selected from 0 to 4,
wherein the method is performed successively without isolation of intermediates.

2. A method for preparing a potassium organotrifluoroborate compound represented by Chemical Formula 1, comprising:
reacting a mixture of a compound represented by Chemical Formula 2 and a borate compound represented by Chemical Formula 5 with an organolithium reagent to prepare a compound represented by Chemical Formula 4; and
reacting the compound represented by Chemical Formula 4 with potassium hydrogen fluoride to prepare the compound represented by Chemical Formula 1:

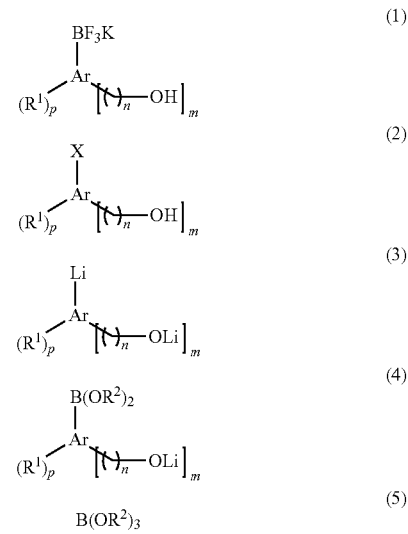

wherein
Ar is selected from phenylene, biphenylene, or naphthylene;
R$^1$ is independently selected from C$_1$-C$_7$ alkyl, C$_1$-C$_7$ alkyloxy, C$_1$-C$_7$ alkylthioxy, hydroxyphenyl, hydroxynaphthyl or halogen;
R$^2$ is selected from C$_1$-C$_7$ alkyl or phenyl;
X is selected from bromine or iodine;
m is an integer selected from 1 to 3;
n is an integer selected from 0 to 4; and
p is an integer selected from 0 to 4.

3. The method for preparing a potassium organotrifluoroborate compound represented by Chemical Formula 1 according to claim 1, wherein the organolithium reagent is selected from n-butyllithium, sec-butyllithium or tert-butyllithium and is used in an amount of 2 to 5 equivalents.

4. The method for preparing a potassium organotrifluoroborate compound represented by Chemical Formula 1 according to claim 1, wherein the borate compound represented by Chemical Formula 5 is selected from trimethylborate ($B(OCH_3)_3$), triethylborate ($B(OCH_2CH_3)_3$), tripropylborate ($B(OCH_2CH_2CH_3)_3$), triisopropylborate ($B(O-{}^iPr)_3$), triisobutylborate ($B(OCH_2-{}^iPr)_3$) or triphenylborate ($B(OPh)_3$) and is used in an amount of 0.9 to 3 equivalents.

5. The method for preparing a potassium organotrifluoroborate compound represented by Chemical Formula 1 according to claim 1, wherein potassium hydrogen fluoride is used in an amount of 2 to 10 equivalents such that the pH of the reaction solution is 4 or lower.

6. The method for preparing a potassium organotrifluoroborate compound represented by Chemical Formula 1 according to claim 1, further comprising, after the preparation of the compound represented by Chemical Formula 1, purifying the compound represented by Chemical Formula 1 using one or more solvent(s) selected from anhydrous acetone, anhydrous methanol, anhydrous ethanol, anhydrous acetonitrile or anhydrous ether.

7. The method for preparing a potassium organotrifluoroborate compound represented by Chemical Formula 1 according to claim 2, wherein the organolithium reagent is selected from n-butyllithium, sec-butyllithium or tert-butyllithium and is used in an amount of 2 to 5 equivalents.

8. The method for preparing a potassium organotrifluoroborate compound represented by Chemical Formula 1 according to claim 2, wherein the borate compound represented by Chemical Formula 5 is selected from trimethylborate ($B(OCH_3)_3$), triethylborate ($B(OCH_2CH_3)_3$), tripropylborate ($B(OCH_2CH_2CH_3)_3$), triisopropylborate ($B(O-{}^iPr)_3$), triisobutylborate ($B(OCH_2-{}^iPr)_3$) or triphenylborate ($B(OPh)_3$) and is used in an amount of 0.9 to 3 equivalents.

9. The method for preparing a potassium organotrifluoroborate compound represented by Chemical Formula 1 according to claim 2, wherein potassium hydrogen fluoride is used in an amount of 2 to 10 equivalents such that the pH of the reaction solution is 4 or lower.

10. The method for preparing a potassium organotrifluoroborate compound represented by Chemical Formula 1 according to claim 2, further comprising, after the preparation of the compound represented by Chemical Formula 1, purifying the compound represented by Chemical Formula 1 using one or more solvent(s) selected from anhydrous acetone, anhydrous methanol, anhydrous ethanol, anhydrous acetonitrile or anhydrous ether.

11. The method for preparing a potassium organotrifluoroborate compound represented by Chemical Formula 1 according to claim 2, which is performed successively without isolation of intermediates.

* * * * *